United States Patent
Pak et al.

(10) Patent No.: US 10,092,593 B2
(45) Date of Patent: *Oct. 9, 2018

(54) CITRATE-RICH CALCIUM-MAGNESIUM SUPPLEMENT AND USES THEREOF

(71) Applicant: THE BOARD OF REGENTS OF THE UNIVERSITY OF TEXAS SYSTEM, Austin, TX (US)

(72) Inventors: Charles Y. C. Pak, Dallas, TX (US); Khashayar Sakhaee, Dallas, TX (US); Orson W. Moe, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 15 days.

This patent is subject to a terminal disclaimer.

(21) Appl. No.: 15/288,210

(22) Filed: Oct. 7, 2016

(65) Prior Publication Data

US 2017/0020921 A1 Jan. 26, 2017

Related U.S. Application Data

(62) Division of application No. 14/425,375, filed as application No. PCT/US2013/057927 on Sep. 4, 2013, now Pat. No. 9,539,283.

(60) Provisional application No. 61/696,662, filed on Sep. 4, 2012.

(51) Int. Cl.

| | |
|---|---|
| *A61K 33/06* | (2006.01) |
| *A61K 31/19* | (2006.01) |
| *A23K 20/24* | (2016.01) |
| *A23L 33/16* | (2016.01) |
| *A23L 2/40* | (2006.01) |
| *A23L 2/52* | (2006.01) |
| *A61K 33/08* | (2006.01) |
| *A61K 33/10* | (2006.01) |
| *A23L 33/00* | (2016.01) |
| *A61K 9/00* | (2006.01) |
| *A61K 9/08* | (2006.01) |
| *A61K 31/194* | (2006.01) |

(52) U.S. Cl.

CPC .............. *A61K 33/06* (2013.01); *A23K 20/24* (2016.05); *A23L 2/40* (2013.01); *A23L 2/52* (2013.01); *A23L 33/16* (2016.08); *A23L 33/30* (2016.08); *A61K 9/0053* (2013.01); *A61K 9/08* (2013.01); *A61K 31/194* (2013.01); *A61K 33/08* (2013.01); *A61K 33/10* (2013.01); *A23V 2002/00* (2013.01); *A23V 2200/00* (2013.01)

(58) Field of Classification Search
None
See application file for complete search history.

(56) References Cited

U.S. PATENT DOCUMENTS

| | | | | |
|---|---|---|---|---|
| 4,814,177 | A | * | 3/1989 | Walsdorf ............. A61K 9/0007 424/464 |
| 2002/0122847 | A1 | * | 9/2002 | Nunes ....................... A23L 2/52 426/72 |
| 2006/0223730 | A1 | | 10/2006 | Neuls et al. |
| 2009/0186939 | A1 | * | 7/2009 | Chan ..................... A61K 9/143 514/502 |
| 2010/0009948 | A1 | | 1/2010 | Nelson et al. |

FOREIGN PATENT DOCUMENTS

| | | |
|---|---|---|
| CN | 101400262 A | 4/2009 |
| WO | 86/04815 | 8/1986 |
| WO | 2008/085728 | 7/2008 |

OTHER PUBLICATIONS

Sarnak, M.J., et al., Kidney Disease as a Risk Factor for Development of Cardiovascular Disease, Circulation, 2003:108:2154-2169, available at http://circ.ahajournals.org/content/108/17/2154).*
Kircelli (Magnesium reduces calcification in bovine vascular smooth muscle cells in a dose-dependent manner, 2012 Nephrol Dial Transplant 27:514-21).*
Bohl et al., "Magnesium and Exercise," Critical Reviews in Food Science and Nutrition, vol. 42, No. 6, 2002, pp. 533-563.
Bolland et al., "Calcium supplements with or without vitamin D and risk of cardiovascular events: reanalysis of the Women's Health Initiative limited access dataset and meta-analysis," Brit. Med. J., vol. 342:d2040, 2011, 9 pages.
Byer et al., "Citrate Provides Protection Against Oxalate and Calcium Oxalate Crystal Induced Oxidative Damage to Renal Epithelium," J. Urol., vol. 173, No. 2, 2005, pp. 640-646.
Cunha et al., "Altered vascular structure and wave reflection in hypertensive women with low magnesium levels," J. Am. Soc. Hyperten., vol. 7, No. 5, 2013, pp. 344-352.
Ewence et al., "Calcium Phosphate Crystals Induce Cell Death in Human Vascular Smooth Muscle Cells: A Potential Mechanism in Atherosclerotic Plaque Destabilization," Circ. Res., 103, 2008, pp. e28-e34.
Hamano et al., "Fetuin-Mineral Complex Reflects Extraosseous Calcification Stress in CKD," J. Am. Soc. Nephrol., vol. 21, 2010, pp. 1998-2007.
Heiss et al., "Fetuin-A Is a Mineral Carrier Protein: Small Angle Neutron Scattering Provides New Insight on Fetuin-A Controlled Calcification Inhibition," Biophy. J., vol. 99, 2010, pp. 3986-3995.
Heller et al., "Pharmacokinetic and Pharmacodynamic Comparison of Two Calcium Supplements in Postmenopausal Women," J. Clin. Pharm., vol. 40, No. 11, 2000, pp. 1237-1244.

(Continued)

*Primary Examiner* — H. Sarah Park
(74) *Attorney, Agent, or Firm* — Norton Rose Fulbright US LLP (57) ABSTRACT

Disclosed is an effervescent preparation of calcium and magnesium with additional citric acid in a defined ratio. Also disclosed is the use of these compositions to raise cardioprotective citrate and magnesium in serum to help prevent heart attacks from calcium supplements, and to provide bioavailable calcium and magnesium to prevent osteoporosis-related fractures and low blood magnesium from the use of proton pump inhibitors.

11 Claims, 6 Drawing Sheets

(56) References Cited

OTHER PUBLICATIONS

Kircelli et al., "Magnesium reduces calcification in bovine vascular smooth muscle cells in a dose-dependent manner," Nephrol. Dialy. Transplant, vol. 27, 2012, pp. 514-521.

Kok et al., "Excessive Crystal Agglomeration with Low Citrate Excretion in Recurrent Stone-Formers," The Lancet, vol. 327, No. 8489, 1986, pp. 1056-1058.

Kuipers et al., "Hypomagnesaemia due to use of proton pump inhibitors—a review," Netherl. J. Med., 67, 2009, pp. 169-172.

Li et al., "Associations of dietary calcium intake and calcium supplementation with myocardial infarction and stroke risk and overall cardiovascular mortality in the Heidelberg cohort of the European Prospective Investigation into Cancer and Nutrition study (EPIC—Heidelberg)," Heart, vol. 98, No. 12, 2012, pp. 920-925.

Montezuno et al., "Vascular Smooth Muscle Cell Differentiation to an Osteogenic Phenotype Involves TRPM7 Modulation by Magnesium," Hypertension, 56:453-462, 2010.

O'Connell et al., "Effects of proton pump inhibitors on calcium carbonate absorption in women: A randomized crossover trial," Am. J. Med., vol. 118, No. 7, 2005, pp. 778-781.

Pak et al., "A model system for assessing physicochemical factors affecting calcium absorbability from the intestinal tract," J. Bone Min. Res., vol. 4, No. 1, 1989, pp. 119-127.

Pak et al., "Enhanced Calcium Bioavailability from a Solubilized Form of Calcium Citrate," J. Clin. Endoc. Metab., vol. 65, No. 4, 1987, pp. 801-805.

Pasch et al., "Nanoparticle-Based Test Measures Overall Propensity for Calcification in Serum," J. Am. Soc. Nephrol., vol. 23, 2012, pp. 1744-1752.

Reid et al., "Cardiovascular effects of calcium supplementation," Osteop. Int., vol. 22, No. 6, 2011, pp. 1649-1658.

Reynolds et al.,"Human Vascular Smooth Muscle Cells Undergo Vesicle-Mediated Calcification in Response to Changes in Extracellular Calcium and Phosphate Concentrations: A Potential Mechanism for Accelerated Vascular Calcification in ESRD," J. Am. Soc. Nephrol., vol. 15, 2004, pp. 2857-2867.

Roux et al., "Increase in Vertebral Fracture Risk in Postmenopausal Women Using Omeprazole," Calcif. Tissue Int., vol. 84, No. 1, 2009, pp. 13-19.

Sage et al., "Hyperphosphatemia-induced nanocrystals upregulate the expression of bone morphogenetic protein-2 and osteopontin genes in mouse smooth muscle cells in vitro," Kid. Int., vol. 79, 2011, pp. 414-422.

International Search Report and Written Opinion in International Application No. PCT/US2013/057927 dated Feb. 10, 2014.

International Preliminary Report on Patentability in International Application No. PCT/US2013/057927 dated Mar. 19, 2015.

Office Action in Chinese Application No. 201380052390.0 dated Dec. 28, 2015.

Search Report in European Application No. 13835639.9 dated Jan. 6, 2016.

Office Action in Chinese Application No. 201380052390.0 dated Feb. 1, 2016.

Examination Report in Australian Application No. 2013312884 dated Mar. 11, 2016.

Office action in Chinese application No. 201380052390.0 dated Sep. 26, 2016.

\* cited by examiner

CITRATE-RICH CALCIUM-MAGNESIUM SUPPLEMENT AND USES THEREOF

CROSS-REFERENCE TO RELATED APPLICATION

This application is a divisional application from U.S. application Ser. No. 14/425,375 filed Mar. 3, 2015, which is a national phase application under 35 U.S.C. § 371 of International Application No. PCT/US2013/057927, filed Sep. 4, 2013, which claims the benefit of priority to U.S. Provisional Patent Application Ser. No. 61/696,662 filed Sep. 4, 2012, the entire contents of each are hereby incorporated by reference.

BACKGROUND

I. Field of the Invention

Disclosed is a composition for a soluble calcium-magnesium preparation, comprised of an effervescent preparation of calcium and magnesium with additional citric acid in a defined ratio. Besides making the product rapidly soluble, the citrate-rich composition ensures adequate increase in serum citrate to attenuate the rise in ionized calcium concentration to help prevent heart attacks. The composition also provides soluble calcium and magnesium to prevent osteoporosis-related fractures and low blood magnesium from the use of proton pump inhibitors (PPIs).

II. Description of the Related Art

Calcium supplements are widely used to supplement the diet to meet recommended dietary allowance and as a concomitant therapy with more specific anti-osteoporosis drugs. It has been traditionally believed that a calcium supplement should be soluble and bioavailable to effectively prevent osteoporosis.

However, a concern has been raised recently that calcium supplements might increase the risk of heart disease and heart attacks by producing a marginal rise in serum calcium (hypercalcemia). Thus, the more bioavailable a calcium supplement, the more likely it might be to cause this complication. Several epidemiological studies revealed an increased risk of heart attacks among subjects taking calcium supplements (Bolland, 2011; Reid, 2011; Li, 2012).

Similarly, magnesium is an important dietary component, touted for a variety of uses, such as avoiding magnesium deficiency, alleviating leg cramps and controlling constipation. Magnesium is also touted to have a beneficial effect on the muscle and heart (Kircelli, 2012). However, available preparations containing both calcium and magnesium are tablet formulations or emulsions with inadequate or poor solubility in water.

Common calcium and magnesium salts require gastric acid to be fully dissolved (Pak, 1989). When gastric acid secretion is blocked by proton pump inhibitors (PPIs), the resulting impairment in the solubility and absorbability of calcium and magnesium salts might increase the risk of osteoporosis-related fractures (Roux, 2009) and hypomagnesemia (Kuipers, 2009) that may cause muscle weakness, lethargy, abnormal heart rhythm, nausea and vomiting.

In conventional calcium supplements, the amount and form of calcium provided to avert bone loss may inappropriately raise serum calcium that might contribute to heart attacks. Furthermore, many conventional supplements of calcium and magnesium are poorly soluble during reduced gastric acid secretion of PPI use, leading to inefficient absorption of these substances. Thus, there remains a need for supplements that provide adequate calcium and magnesium in amounts and forms that are effective to achieve the benefits (prevention of bone loss during calcium supplements; avoidance of osteoporosis-related fractures and hypomagnesemia during PPI use) without adverse effects (heart attacks from calcium supplements).

SUMMARY OF THE INVENTION

The current problem in calcium supplementation is to accommodate two opposing influences. To avert bone loss, calcium bioavailability must be optimal to suppress parathyroid function. However, optimum calcium absorption could raise serum calcium that might lead to heart attacks. In some aspects of the present invention, this problem is overcome by a new composition that not only assures efficient solubility and optimum calcium bioavailability, but also raises serum citrate and magnesium to reduce cardiovascular risk. Moreover, this composition provides soluble calcium and magnesium that is ideal for the prevention of osteoporosis-related fractures and hypomagnesemia from PPI.

In some aspects, the present invention provides a composition comprising a mixture comprising calcium, magnesium, and citrate excess, with high total citrate. In some embodiments, the calcium is calcium carbonate, calcium hydroxide, calcium citrate, or calcium oxide. In some embodiments, the calcium is calcium carbonate. In some embodiments, the magnesium is magnesium citrate or magnesium hydroxide. In some embodiments, the magnesium is magnesium citrate. In some embodiments, the citrate is citric acid.

In some embodiments, the present invention provides a composition comprising a mixture comprising from about 250 mg calcium to about 600 mg calcium, from about 70 mg magnesium to about 175 mg magnesium, at least 10 meq (milliequivalents) of citrate excess, and at least 20 meq of total soluble citrate, wherein the Ca/citrate molar ratio is from 0.4 to 0.7. In some embodiments, the composition comprises 400 mg of calcium, 122 mg of magnesium, 20 meq of citrate excess, and 50 meq (16.7 millimoles or mmol) of total soluble citrate, wherein the Ca/citrate molar ratio is about 0.6. In some embodiments, the composition consists essentially of 400 mg (20 meq) of calcium, 122 mg of magnesium (10 meq), 20 meq of citrate excess, and 50 meq of total soluble citrate, wherein the Ca/citrate molar ratio is 0.6 (400 mg calcium=10 mmol; 50 meq citrate=16.7 mmol; Ca/citrate molar ratio=10/16.6=0.6).

The composition may be in any appropriate form. In some embodiments, the mixture is in the form of a tablet. In some embodiments, the mixture is in the form of a powder.

In another aspect, the present invention provides a method of preventing or treating osteoporosis, osteomalacia, or low blood calcium in an animal in need of such treatment comprising obtaining a dose of any of the disclosed compositions and administering the dose to the animal, wherein the osteoporosis, osteomalacia, rickets, or low blood calcium is treated in the animal. In some embodiments, the animal is a human.

In another aspect, the present invention provides a method of preventing fragility fractures and magnesium deficiency in an animal in need of such treatment comprising obtaining a dose of any of the disclosed compositions and administering the dose to the animal, wherein osteoporosis-related fractures and hypomagnesemia are treated in the animal. In some embodiments, the animal takes inhibitors of gastric acid secretion. In some embodiments, the animal is a human.

In another aspect, the present invention provides a method of reducing cardiovascular risk from calcium supplementation in an animal in need thereof comprising obtaining a dose of any of the disclosed compositions and administering the dose to the animal, wherein the cardiovascular risk is reduced in the animal. In some embodiments, the animal is a human. The reduction of cardiovascular risk may be demonstrated by a reduction in symptoms indicative of heart attacks or heart failure, such as chest pain, shortness of breath, abnormal heart rhythm, and swelling in the legs. In some embodiments, the reduction of cardiovascular risk is demonstrated by less likelihood of suffering from heart attacks or heart failure. In some embodiments, the composition is capable of reducing cardiovascular risk by providing citrate and magnesium load, raising serum citrate and magnesium, and retarding formation of calciprotein particles (CPP) that can initiate vascular calcification. In some embodiments, the rapid solubility of the composition provides soluble load of citrate and magnesium.

The composition may be administered in any suitable manner. For example, it may be administered intravenously, intraarterially, intralesionally, intranasally, intravaginally, intrarectally, topically, intratumorally, systemically, intravesicularly, mucosally, orally, locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 1990). In some embodiments, administration comprises oral administration.

In some embodiments, the composition is further defined as an aqueous solution. In some embodiments, the method may further comprise preparing the aqueous solution by dissolving the dose comprising the mixture in water. In some embodiments, the solution elaborates carbon dioxide upon dissolution.

The composition may be administered to (or taken by) the patient 1, 2, 3, 4, 5, 6, 7, 8, 9, 10, 11, 12, 13, 14, 15, 16, 17, 18, 19, 20 or more times, or any range derivable therein, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or 1, 2, 3, 4, 5, 6, 7, 8, 9, 10 years, or longer, or any range derivable therein. It is specifically contemplated that the composition may be administered once daily, twice daily, three times daily, four times daily, five times daily, or six times daily (or any range derivable therein) and/or as needed to the patient. Alternatively, the composition may be administered every 2, 4, 6, 8, 12 or 24 hours (or any range derivable therein) to or by the patient. It is specifically contemplated that the composition may be administered daily over the course of multiple years.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Effective amount" or "therapeutically effective amount" or "pharmaceutically effective amount" means that amount which, when administered to a subject or patient for treating a disease, is sufficient to effect such treatment for the disease. In some embodiments, the subject is administered at least about 5, 6, 7, 8, 9, 10, 20, 30, 40, 50, 60, 70, 80, 90, 100, 110, 120, 130, 140, 150, 160, 170, 180, 190, or 200 mg/kg or mg/kg/dose or more or any range derivable therein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, the words "consisting essentially of" encompass the specified materials or steps and those additional components that do not materially affect the basic and novel characteristics of the claimed invention.

Descriptions of well-known processing techniques, components, and equipment are omitted so as not to unnecessarily obscure the present methods and devices in unnecessary detail. Other objects, features and advantages of the present invention will become apparent from the following detailed description. It should be understood, however, that the detailed description and the specific examples, while indicating specific embodiments of the invention, are given by way of illustration only, as various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4 shows intestinal calcium absorption from a single oral load of EffCaMgCit or calcium carbonate ($CaCO_3$) on the $7^{th}$ day of treatment with omeprazole (OMP) or placebo in 11 adult men or women. EffCaMgCit load contained 400 mg calcium, 122 mg magnesium, and 50 meq of citrate. Ca carbonate load contained 400 mg calcium, but no magnesium or citrate. Subjects underwent four phases of study in a crossover randomized design, comprised of EffCaMgCit after placebo (designated as minus or −OMP), EffCaMgCit after OMP (designated as +OMP), calcium carbonate after placebo (−OMP), and calcium carbonate after OMP (+OMP). During OMP phases, a state of low gastric acid secretion was created by treatment with omeprazole, a commonly used PPI. There was at least two weeks of "recovery" between phases. Intestinal calcium absorption was measured from the cumulative increment in serum calcium from baseline (delta area under the curve, or $\Delta AUC$ of serum calcium) over 6 hours following test loads by a well-established technique (Heller, 2000).

DETAILED DESCRIPTION OF THE INVENTION

Disclosed herein is a new composition for a soluble calcium-magnesium preparation, comprised of an effervescent preparation of calcium and magnesium with additional citric acid in a defined ratio, designed to serve three purposes. First, the unique composition ensures rapid solubility and absorbability of calcium, magnesium and citrate from the bowel. Second, by providing optimally absorbed citrate and magnesium, the composition raises serum citrate and magnesium to help prevent heart attacks that is associated with calcium supplementation. Third, the composition provides absorbable calcium and magnesium even in a state of defective gastric acid secretion to help prevent osteoporosis-related fractures and low blood magnesium (hypomagnesemia) during the use of proton pump inhibitors (PPI), a commonly used over-the-counter medicine.

A. Effervescent Calcium Magnesium Citrate

In one aspect, the present invention relates to an effervescent calcium magnesium citrate (EffCaMgCit), which is a powder mix of calcium carbonate, magnesium citrate and citric acid in a well-defined ratio. In some embodiments, the composition is intended to be dissolved in water before oral ingestion. To obtain a customary, clinically effective dose of calcium (from 250 mg to 600 mg per unit dose) and magnesium (from 70 mg to 175 mg per unit dose), EffCaMgCit contains at least 10 meq of citrate excess and at least 20 meq of total soluble citrate per unit dose, to yield Ca/citrate molar ratio equal to or less than 0.7. This amount of citrate ensures a desired rise in serum citrate to reduce the risk of heart attacks from calcium supplementation. This molar ratio in addition to the additional citrate assures a rapid and full solubility of the composition in water to provide soluble citrate and magnesium (useful in preventing heart attacks), as well as calcium and magnesium (useful in preventing osteoporosis-related fractures and hypomagnesemia from PPI). In particular embodiments, EffCaMgCit contains 400 mg calcium per unit dose, 122 mg magnesium per unit dose, 20 meq citrate excess and total citrate of 50 meq per unit dose, and Ca/citrate molar ratio of 0.6.

To make EffCaMgCit, a solid powder preparation of poorly soluble calcium carbonate is added to water, along with magnesium citrate and citric acid. This mixture elaborates carbon dioxide gas as it rapidly dissolves; thus, the poorly soluble calcium carbonate is rendered readily soluble. The use of a powder mixture of calcium, magnesium and citrate that dissolves rapidly and fully, permitting ingestion as a liquid is beneficial. For example, some patients prefer to drink a liquid preparation rather than swallow tablets. The rapidity with which the powder formulations dissolve overcomes the problem of somewhat poor solubility of tablet formulations.

EffCaMgCit contains additional citric acid to yield a calcium/citrate molar ratio of 0.6. Calcium supplements in the marketplace have a much higher Ca/citrate molar ratio, with a value of infinity for calcium carbonate and calcium phosphate, and 1.5 for calcium citrate. This is illustrated in Table 1. EffCaMgCit also has a greater citrate excess (20 meq per unit dose) than conventional preparations. These properties provide rapid and complete solubility of the composition.

TABLE 1

Ca/Cit Molar Ratios of Ca—Mg Preparations
(Corrected to 400 mg Ca per dose/serving as in EffCaMgCit)

| | Calcium | Citrate | Ca/Citrate (molar) | Citrate Excess | Medium | Solubility | Effervescence |
|---|---|---|---|---|---|---|---|
| Liquid Preparations | | | | | | | |
| EffCaMgCit (Mg = 122 mg) | 400 mg 10 mmol | 50 meq 16.67 mmol | 0.6 | 20 meq | 240 ml water | Rapid Complete | Yes |
| Orange Juice + Ca (Mg = 34 mg; K = 15 meq) | 400 mg 10 mmol | 35.3 meq 11.8 mmol | 0.85 | 1 meq | 274 ml product | Pre-solubilized | No |
| CaCit (France) Mg = 0 | 400 mg 10 mmol | 24 meq 8 mmol | 1.25 | 4 meq | 240 ml water | Slow Complete | Yes |

TABLE 1-continued

Ca/Cit Molar Ratios of Ca—Mg Preparations
(Corrected to 400 mg Ca per dose/serving as in EffCaMgCit)

| | Calcium | Citrate | Ca/Citrate (molar) | Citrate Excess | Medium | Solubility | Effervescence |
|---|---|---|---|---|---|---|---|
| Mail Order Emulsions | | | | | | | |
| Integrated Therapeutics Liquid CaMg:vanilla (Mg = 334 mg) 11120517; LI206012.03 | 400 mg 10 mmol | 0 | Infinity | 0 | ~0.5-1 oz product | Emulsion Incomplete | No |
| Lifetime Liquid CaMgCit, Orange-vanilla #2941-C2 (Mg = 143 mg) | 400 mg 10 mmol | 41.1 meq 13.7 mmol | 0.73 | 9.3 meq | ~0.5-1 oz product | Emulsion Incomplete | No |
| Lifetime Liquid CaMgCit Blueberry #2982-C2 15:35:16 (Mg = 157 mg) | 400 mg 10 mmol | 37.8 meq 12.6 mmol | 0.79 | 5 meq | ~0.5-1 oz product | Emulsion Incomplete | No |
| Bluebonnet Liquid CaMg Cit Blueberry #3472-A2 15:41:37 (Mg = 196 mg) | 400 mg 10 mmol | 42.3 meq 14.1 mmol | 0.71 | 6.2 meq | ~0.5-1 oz product | Emulsion Incomplete | No |
| Solgar Liquid CaMgCit Strawberry #3191-B2 08:49:37 (Mg = 196 mg) | 400 mg 10 mmol | 43.1 meq 14.4 mmol | 0.70 | 7 meq | ~0.5-1 oz product | Emulsion Incomplete | No |
| Tropical Oasis Liquid CaMgCit, Orange (Mg = 140 mg) 17279 34002 | 400 mg 10 mmol | 39.2 meq 13.1 mmol | 0.77 | 7.9 meq | ~0.5-1 oz product | Emulsion Incomplete | No |
| Tablet Preparations | | | | | | | |
| Citracal Regular (Mg = 0) | 400 mg 10 mmol | 20 meq 6.67 mmol | 1.5 | 0 | 240 ml water | Slow Modest | No |
| Ca Carbonate (Mg = 0) | 400 mg 10 mmol | 0 | Infinity | 0 | 240 ml water | Slow Poor | No |
| Ca Phosphate (Mg = 0) | 400 mg 10 mmol | 0 | Infinity | 0 | 240 ml water | Slow Poor | No |
| Ca Acetate (Mg = 0) | 400 mg 10 mmol | 0 | Infinity | 0 | 240 ml water | Slow Modest | No |
| Citracal + Mg (Mg = 64 mg) | 400 mg 10 mmol | 20 meq 6.67 mmol | 1.5 | 0 | 240 ml water | Slow Modest | No | mmol = millimoles;
meq = milliequivalents

Moreover, EffCaMgCit has citrate excess or free citrate of 20 meq citrate per unit dose (total citrate minus total calcium+magnesium; 50–20–10=20). The total soluble citrate from a single dose of EffCaMgCit is 50 meq (=20 meq from calcium citrate, 10 meq from magnesium citrate and 20 meq from citric acid). Since EffCaMgCit is completely solubilized in water before ingestion, all of its content of citrate contributes to total soluble citrate. That is not the case with tablet formulations of calcium citrate that are partially soluble. Furthermore, since EffCaMgCit contains 50 meq of total soluble citrate per unit dose and 20 meq of free citrate, it can elicit a rise in serum citrate comparable or superior to that of 40 meq citric acid.

The composition of EffCaMgCit possesses not only a low Ca/citrate ratio but also contains sufficient free citrate and total free citrate. A low Ca/citrate molar ratio alone does not ensure efficient solubility or satisfactory citratemic response (rise in serum citrate), unless it is accompanied by adequate citrate excess (see emulsions, Table 1). Thus, all 6 mail order preparations of calcium magnesium citrate (with low citrate excess) remained as an emulsion even when the recommended dose unit of 0.5-1 oz was diluted to 240 ml with water. The amount of free and total soluble citrate contained in EffCaMgCit is designed to attenuate the expected rise in serum ionized calcium from the unit dose of calcium 400 mg. When a higher unit dose of calcium is to be used, the amount of free citrate and total soluble citrate must be adjusted to maintain the Ca/citrate molar ratio low.

Based on the needs of average healthy individuals, it is believed that the optimal amounts per unit dose of EffCaMgCit are: (a) calcium 400 mg, to provide optimum calcium bioavailability without provoking hypercalcemia, (b) magnesium 122 mg, to offer bioavailable magnesium without provoking diarrhea, (c) Ca/citrate molar ratio of 0.6, (d) citrate excess of 20 meq, and (e) total soluble citrate of 50 meq per unit dose. However, other dosages may be effective. For example, in persons with defective intestinal calcium absorption, a higher amount of calcium might be desired. This would necessitate appropriate changes in free citrate and total soluble citrate. Alternatively, in patients with absorptive hypercalciuria suffering from kidney stones due to high intestinal calcium absorption, a lower unit dose of calcium might be preferred, while maintaining the same citrate excess and total soluble citrate. Persons skilled in the art might modify the amounts of various components of the composition, depending on circumstances, individual needs and conditions.

B. Cardioprotection by EffCaMgCit

Patients on calcium supplementation rarely sustain a rise in serum calcium concentration approaching the upper normal limit (Heller, 2000). However, it is possible that a transient marginal hypercalcemia might ensue intermittently often enough over months or years of supplementation to potentially damage the coronary arteries (Reid, 2011). Hypercalcemia might raise the saturation of calcium phosphate in serum, causing formation of inorganic calcium phosphate. Inorganic calcium phosphate then agglomerates with fetuin to form calciprotein particles (CPP), previously called calcium phosphate nanoparticles (CP-NP) (Heiss, 2010). In chronic kidney disease where high serum phosphate is commonly encountered to increase saturation of calcium phosphate, CPP has been detected in serum and found to correlate with coronary artery calcification (Hamano, 2010). CPP might damage vascular endothelial cells, and cause apoptosis (cell death), osteogenic transformation (conversion to bone-forming cells), and calcification (akin to bone formation) of vascular smooth muscle cells (as in coronary arteries) (Pasch, 2012; Sage, 2011; Ewence, 2008).

EffCaMgCit confers protection against heart attacks by providing soluble citrate and magnesium that are cardioprotective. Turning to the role of citrate first, EffCaMgCit has unique characteristics designed to protect the heart apart from provision of magnesium: a Ca/citrate molar ratio of 0.6, additional citric acid (citrate minus calcium and magnesium) of 20 meq (also called "citrate excess" or "free citrate") and soluble total citrate of 50 meq per unit dose. Thus, even though calcium is optimally absorbed from this preparation, the disclosed formulation uniquely provides a sufficient amount of free and total citrate to increase serum citrate to complex calcium. This action blunts the rise in serum ionized calcium that might damage the heart (Reid, 2011). As one way, the blunted rise in serum ionized calcium helps to prevent the serum from becoming overly supersaturated with respect to calcium phosphate, averting the formation of CPP that might initiate vascular calcification (Reynolds, 2009; Hamano, 2010; Sage, 2011). There might be other ways oral delivery of soluble citrate might retard appearance of CPP in blood. Secondly, through its physicochemical action as an "inhibitor" of calcification and agglomeration (Kok, 1986), citrate might directly inhibit formation of CPP. Thirdly, a rise in serum citrate might be cardioprotective through citrate's antioxidant action (Byer, 2005).

Now to the cardioprotective role of magnesium, EffCaMgCit delivers 10 meq (122 mg) of magnesium per unit dose. In vascular smooth muscle cells, magnesium has been shown to inhibit calcium deposition and avert cell death (Kircelli, 2012), and increase the expression of factors that inhibit calcification (Montezuno, 2010). In human beings, low serum magnesium has been reported to be associated with higher blood pressure and abnormal vascular function (Cunha, 2013).

Magnesium is also considered an inhibitor of calcium phosphate precipitation/crystallization. The formation of CPP in vitro has been shown to be inhibited by magnesium (Pasch, 2012). In the bowel, magnesium might impair absorption of phosphate, thus attenuating the rise in serum phosphate that could promote CPP formation and be harmful to the heart. Thus, magnesium provided with EffCaMgCit confers cardiovascular protection.

Figure 1:
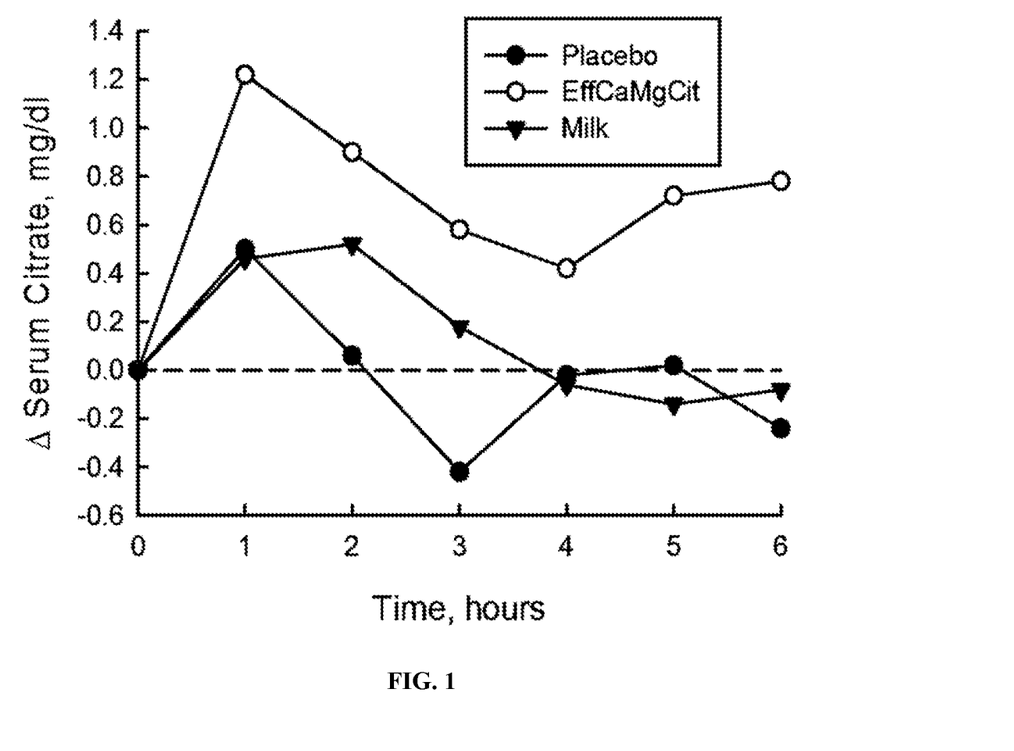
FIG. 1 illustrates serum citrate concentration over 6 hours after a single oral load of effervescent calcium magnesium citrate (EffCaMgCit) (open circle), milk (inverted triangle) or placebo (closed circle) in 12 healthy women. EffCaMgCit load contained 400 mg (20 meq) calcium, 122 mg (10 meq) magnesium, and 50 meq of citrate. Milk (about 400 ml of 2% organic milk) contained 400 mg calcium, 40 mg (3.3 meq) magnesium, and 8.4 meq of citrate. The figure depicts change in serum citrate from baseline (time zero, Δ serum citrate) over 6 hours after the oral test loads.
Figure 2:
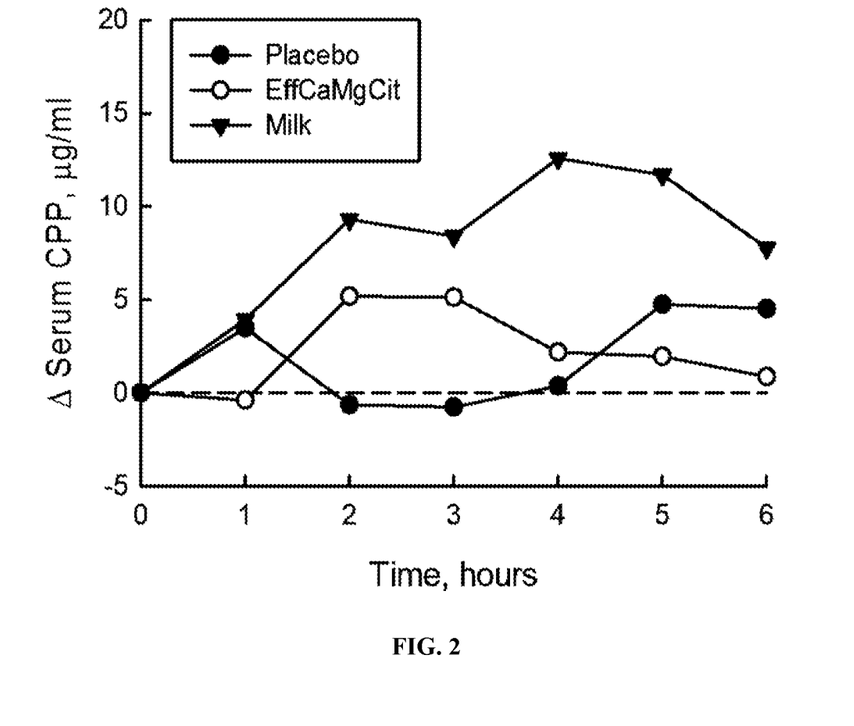
FIG. 2 shows serum concentration of calciprotein particles (CPP), formerly called calcium phosphate nanoparticles (CP-NP), after a single oral load of EffCaMgCit (open circle), milk (inverted triangle) or placebo (closed circle) in 10 healthy women (available so far from the same study as in FIG. 1). The change in serum CPP from baseline (Δ serum CPP) over 6 hours after the test loads is presented. CPP is expressed as hydroxyapatite equivalent/ml.

The Examples presented below demonstrate that EffCaMgCit increases serum citrate (FIG. 1) and soluble calcium citrate complex (Table 5), raises serum magnesium (FIG. 5), and inhibits the appearance of CPP in serum (FIG. 2).

C. Prevention of Skeletal Fractures and Hypomagnesemia during Proton Pump Inhibitor Therapy Proton pump inhibitors (PPI) are suspected as causing skeletal fractures (Roux, 2009) and severe hypomagnesemia (Kuipers, 2009). PPI produces hypochlorhydria (reduced) or achlorhydria (absent gastric acid secretion). Common calcium and magnesium salts require gastric acid for full solubility (Pak, 1989). Thus, a plausible explanation for the above complications of PPI is the induction of hypo- or achlorhydria that impairs the solubility and hence the bioavailability of calcium (O'Connell, 2005) and magnesium salts (Kuipers, 2009). Impaired calcium absorption would cause parathyroid stimulation and bone loss. Poor magnesium absorption would produce hypomagnesemia.

The effect of PPI on the bioavailability of calcium (and magnesium) from a given supplement is thought to be dependent on the initial state of solubility of that supplement. Thus, in the case of a poorly soluble calcium salt (such as calcium carbonate), the inhibition of gastric acid secretion by PPI may preclude an adequate solubility and calcium absorbability. On the other hand, the calcium bioavailability of an already solubilized calcium preparation (such as EffCaMgCit) should not be affected as much by impaired gastric acid secretion from PPI (Pak, 1987). The same applies for magnesium bioavailability. EffCaMgCit is advantageous, since it delivers soluble magnesium. A special advantage of EffCaMgCit is that it provides both soluble calcium and soluble magnesium in a single preparation; hence its calcium and magnesium bioavailability is not so dependent on gastric acid secretion.

The Examples below demonstrate that EffCaMgCit confers optimum bioavailability of calcium (FIG. 4) and magnesium (FIG. 5) and provides adequate parathyroid suppression (FIG. 6), even following inhibition of gastric acid secretion by omeprazole, a commonly used PPI.

D. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. In particular, Examples 1 and 2 are laboratory studies showing unique composition and solubility of EffCaMgCit. Examples 3, 4 and 5 are concerned with cardioprotection from calcium supplements conferred by EffCaMgCit, and Examples 6, 7 and 8 are concerned with the value of EffCaMgCit during PPI treatment.

Example 1

Enhanced Solubility of EffCaMgCit by Using Magnesium Citrate Instead of Magnesium Hydroxide, and by Additional Citric Acid The unit dose were dissolved completely in 8 ounces (oz) serving of water within 2 minutes. Three preparations of effervescent calcium magnesium citrate at a unit dose delivering 400 mg calcium were tested. All preparations contained calcium carbonate containing 400 mg (20 meq) calcium. Preparation A utilized magnesium hydroxide delivering 122 mg (10 meq) magnesium. It contained 40 meq of citric acid, delivering a slight citrate excess of 10 meq (=40 meq citrate minus 20 meq Ca+10 meq Mg) and total soluble citrate of 40 meq (Table 2).

TABLE 2

Preparation A: Contents of Unit Dose

| | mmol/ sachet | mg/ sachet | mg Ca/ unit dose (meq) | mg Mg/ unit dose (meq) | meq Citrate/ unit dose |
|---|---|---|---|---|---|
| CaCO$_3$ | 10 | 1,001 | 400 (20) | 0 | 0 |
| Mg(OH)$_2$ | 5 | 292 | 0 | 122 (10) | 0 |
| Citric Acid•H$_2$O | 13.33 | 2,801 | 0 | 0 | 40 |
| Total | | 4,094 | 400 (20) | 122 (10) | 40 |

Solubility and taste test was done blindly by the main inventor and his four colleagues. Preparation A went into a suspension with effervescence when added to 8 oz water. In 20 minutes, the preparation was still cloudy, though with little remaining effervescence. It took 30 minutes to clear. Taste was flat, though without aftertaste.

Preparation B also contained magnesium hydroxide, but included a larger amount of citric acid to yield citrate excess of 20 meq per unit dose (=50 meq citrate minus 20 meq calcium+10 meq magnesium), and total soluble citrate of 50 meq (Table 3). When added to 8 oz water, this preparation had a greater effervescence than Preparation A. It was still cloudy in 10 minutes. It was clear in about 25 minutes. It was slightly tart. Three of 5 persons preferred the taste of this preparation over Preparation A. Thus, a larger amount of citric acid (greater citrate excess) shortened the dissolution time and improved the taste.

TABLE 3

Preparation B: Contents of Unit Dose

| | mmol/ packet | mg/ packet | mg Ca/ unit dose (meq) | mg Mg/ unit dose (meq) | meq Citrate/ unit dose |
|---|---|---|---|---|---|
| CaCO$_3$ | 10 | 1,001 | 400 (20) | 0 | 0 |
| Mg(OH)$_2$ | 5 | 292 | 0 | 122 (10) | 0 |
| Citric Acid•H$_2$O | 16.66 | 3,501 | 0 | 0 | 50 |
| Total | | 4,794 | 400 (20) | 122 (10) | 50 |

In Preparation C (one embodiment of EffCaMgCit), magnesium citrate replaced magnesium hydroxide (Table 4). A higher citrate excess of 20 meq per unit dose (with the same total soluble citrate of 50 meq) was used as in Preparation B. This preparation went into solution with active effervescence. In 1 minute, it was only slightly cloudy. In 2 minutes, it was completely clear. Its taste was similar to that of Preparation B.

TABLE 4

Preparation C: Contents of Unit Dose

| | mmol/ packet | mg/ packet | mg Ca/ unit dose (meq) | mg Mg/ unit dose (meq) | meq Citrate/ unit dose |
|---|---|---|---|---|---|
| CaCO$_3$ | 10 | 1,001 | 400 (20) | 0 | 0 |
| Mg$_3$Citrate$_2$ | 1.67 | 752 | 0 | 122 (10) | 10 |
| Citric Acid•H$_2$O | 13.33 | 2,801 | 0 | 0 | 40 |
| Total | | 4,554 | 400 (20) | 122 (10) | 50 |

In conclusion, the solubility of calcium magnesium citrate was enhanced by using magnesium citrate rather than magnesium hydroxide, and by a moderate degree of citrate excess.

Unique compositional features of EffCaMgCit (Preparation C) are: Ca/citrate molar ratio of 0.6, citrate excess or free citrate of 20 meq, and total soluble citrate of 50 meq. This admix also delivers effective and safe amounts of calcium (400 mg) and magnesium (122 mg) per unit dose. Ample citrate excess and total soluble citrate, combined with the use of magnesium citrate instead of magnesium hydroxide, permit rapid solubility of the composition with a satisfactory taste.

Example 2

Comparison of Ca/Citrate Molar Ratio and Citrate Excess between EffCaMgCit and other Representative Calcium Preparations Analysis of other representative calcium preparations revealed that their Ca/citrate molar ratio is higher and citrate excess is lower than EffCaMgCit (Preparation C). Table 1 (above) compares the composition and properties of EffCaMgCit with those of calcium-fortified orange juice and effervescent calcium citrate (CaCit, marketed in France). A unit dose containing 400 mg calcium also delivers a modest amount of magnesium (122 mg) from EffCaMgCit, a small (subclinically effective) amount from Ca-fortified orange juice (34 mg) and none from CaCit. Thus, only EffCaMgCit qualified as a true Ca—Mg preparation. Ca-fortified orange juice is pre-solubilized, whereas the other two are effervescent preparations. When placed in water, EffCaMgCit dissolves rapidly (within two minutes), but CaCit dissolves more slowly. EffCaMgCit has the lowest Ca/citrate molar ratio at 0.6 and highest citrate excess of 20 meq per unit dose. While Ca-fortified orange juice has a slightly higher Ca/citrate molar ratio of 0.85, it has a much lower citrate excess of 1 meq. CaCit has a much higher Ca/citrate molar ratio of 1.25 and much lower citrate excess of 4 meq. Ca-fortified orange juice has moderately high potassium content of 15 meq per single load, which for a calcium supplement would require an approval from the FDA as a prescription drug.

Six formulations listed as "liquid" calcium magnesium citrate were purchased by mail order, and their composition analyzed (Table 1). Compositions were corrected for a unit dose delivering 400 mg calcium. Magnesium content varied from 140-334 mg. One preparation (Integrated Therapeutics) contained no citrate, yielding a Ca/citrate molar ratio of infinity and citrate excess of zero. The remaining five formulations had modest citrate content, giving Ca/citrate molar ratio slightly higher than that of EffCaMgCit (0.70-0.79 versus 0.6). However, citrate excess was much lower for these formulations than EffCaMgCit (5-9 meq versus 20 meq). All six formulations were emulsions with incomplete or poor solubility without effervescence.

Compositions of 5 (tablet) commercial calcium supplements are compared in Table 1 at a unit dose delivering 400 mg calcium. None contained magnesium except Citracal+Mg. The two Citracal preparations contained citrate, yielding Ca/citrate molar ratio of 1.5, but zero citrate excess. Calcium carbonate, calcium phosphate and calcium acetate tablets did not contain any citrate, giving Ca/citrate ratio of infinity and zero citrate excess. None were effervescent formulations. Calcium citrate and calcium acetate have a modest solubility, but calcium carbonate and calcium phosphate have poor solubility in water (Pak, 1989).

In conclusion, EffCaMgCit (Preparation C) is unique among representative calcium preparations, by virtue of having both a lower Ca/citrate molar ratio (of 0.6) and greater citrate excess (of 20 meq). These properties assure superior solubility of EffCaMgCit over conventional preparations. EffCaMgCit is unique in providing optimum amounts of soluble calcium, magnesium and citrate in a single preparation.

Example 3

Increased Serum Citrate Concentration after a Single Oral Load of EffCaMgCit

In this cardioprotection protocol, the effect of EffCaMgCit on serum citrate concentration was compared with that of milk and placebo, to test the hypothesis that EffCaMgCit confers a greater citratemic response than milk or placebo. 12 healthy adult women completed a crossover single dose bioavailability study, wherein serum citrate was measured before and for 6 hours after a single oral dose of EffCaMgCit, milk or placebo. EffCaMgCit contained 400 mg (20 meq) calcium, 122 (10 meq) mg magnesium and 50 meq citrate. Milk contained 400 mg calcium, 40 mg (3.3 meq) magnesium, and 8.4 meq of citrate. Placebo was devoid of calcium, magnesium or citrate. There was at least a week of "withdrawal period" between test loads.

In each bioavailability study, the test load was given at 8 a.m. with a standard breakfast meal after an overnight fast. A venous blood sample was obtained before the test load, and at hourly intervals for 6 hours after the oral test dose. Serum samples were measured for citrate. The rise in serum citrate from baseline yielded a measure of intestinal citrate absorption.

FIG. 1 illustrates the change in serum citrate after oral test loads. Serum citrate rose rapidly reaching the peak during the first hour after EffCaMgCit load; it remained above baseline during the remaining 5 hours. Serum citrate rose modestly after ingestion of milk (about one-half the rise after EffCaMgCit) during the first three hours after ingestion of milk. Serum citrate increased only during the first hour after placebo. Change in area under the curve from baseline of serum citrate (ΔAUC), a quantitative measure of citrate absorption, was significantly different between the three phases by ANOVA (p=0.05). ΔAUC of EffCaMgCit was significantly higher than milk (p=0.05) or placebo (p=0.02). Thus, EffCaMgCit confers a greater citrate bioavailability and citratemic response than milk, a standard calcium-rich food.

Citrate forms soluble complexes with calcium in serum, prominent ones being $CaCit^-$ and $CaCitPO_4^{4-}$ (calcium phosphocitrate). From the serum citrate following a single oral load of EffCaMgCit described in FIG. 1, the JESS program computed calcium citrate complexes by using known association constants. Table 5 displays the sum of all calcium citrate complexes (CaCit Complexes) in serum before and at hourly intervals over 6 hours after a single oral dose of EffCaMgCit. The change from baseline (Δ CaCit Complexes) is also shown.

TABLE 5

| | Ca-Citrate Complexes | | | | | | |
|---|---|---|---|---|---|---|---|
| | Duration Post-Load, hr | | | | | | |
| | 0 | 1 | 2 | 3 | 4 | 5 | 6 |
| Citrate, mmol/L | 0.188 | 0.252 | 0.235 | 0.219 | 0.210 | 0.226 | 0.229 |
| CaCit Complexes | 0.089 | 0.119 | 0.113 | 0.105 | 0.102 | 0.110 | 0.112 |
| Δ CaCit Complexes | 0.000 | 0.030 | 0.024 | 0.016 | 0.013 | 0.021 | 0.023 |

As shown in Table 5 and FIG. 1, serum citrate rose prominently during the first hour after a single oral dose of EffCaMgCit, and remained higher than baseline during the remaining five hours. Commensurate with this rise, total soluble calcium citrate complexes increased at the same times.

Serum ultrafiltrable calcium is a sum of complexed calcium and ionized calcium. The above increase in total calcium citrate complexes from the citratemic response to EffCaMgCit load therefore reduces the ionized calcium fraction. Thus, the rise in serum citrate from EffCaMgCit blunts the increase in ionized calcium fraction from the calcium load. Since it is the ionized serum calcium rather than total calcium that is presumed to be responsible for cardiotoxicity, the rise in serum citrate is likely to be cardioprotective.

EffCaMgCit also increased serum magnesium concentration. To be described in Example 7 and FIG. 5 from the PPI protocol, EffCaMgCit provided bioavailable magnesium, measured from the cumulative increment in serum magnesium concentration from baseline following a single oral load.

Example 4

Reduced CPP Formation in Serum by EffCaMgCit

In the same cardioprotection protocol as in Example 3, serum samples were analyzed for calciprotein particles (in the laboratory of M. Kuro-o). In samples from 10 subjects so far analyzed, serum CPP concentration rose modestly from baseline over 6 hours after an oral load of milk (FIG. 2). However, after EffCaMgCit load, serum CPP was slightly higher than at baseline at 2 and 3 hours but not at 4-6 hours. The increment in serum CPP from baseline (delta area under the curve or ΔAUC) for milk was about 5-fold that of placebo, but ΔAUC for EffCaMgCit was only 1.5-fold that of placebo. Despite low power (n=10), the difference in Δ CPP was marginally significant between milk and placebo (p=0.12) and between EffCaMgCit and milk (p=0.17). Seven of 10 subjects ingesting milk had a serum CPP value over 20 μg/ml at least once, whereas only 2 subjects taking EffCaMgCit did. Thus, CPP, a factor that might initiate vascular calcification, is less likely to form in serum following EffCaMgCit than after milk.

Example 5

Parathyroid Suppression by EffCaMgCit

Figure 3:
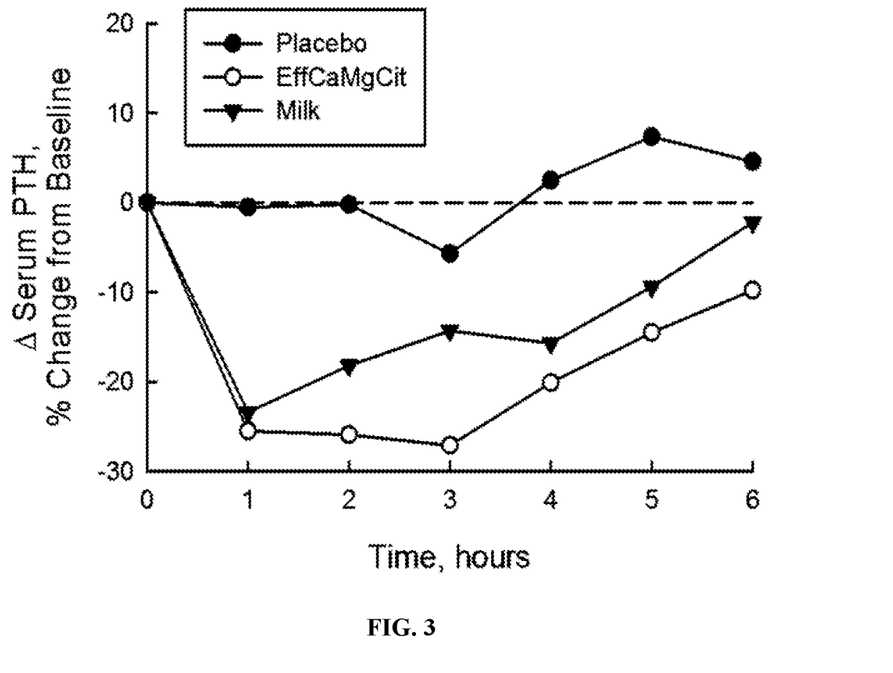
FIG. 3 shows percent change in serum parathyroid hormone (PTH) concentration from baseline (Δ serum PTH) over 6 hours after a single oral load of EffCaMgCit (open circle), milk (inverted triangle) or placebo (closed circle) in 12 healthy women (same study as in FIG. 1). A negative value indicates parathyroid suppression.

In the same cardioprotection protocol as Example 3, serum samples were measured for PTH before and during 6 hours after oral test loads. The decline in serum PTH from baseline yielded a measure of parathyroid suppression. FIG. 3 depicts percent change in serum PTH from baseline (Δ serum PTH), where a negative value indicated parathyroid suppression. After EffCaMgCit load, serum PTH declined at 1 hour and remained suppressed for 5 hours. After milk load, serum PTH declined to a similar degree as with EffCaMgCit load at 1 hour after load; this decline was less marked with milk than with EffCaMgCit during the subsequent 5 hours. There was no substantial change in Δ serum PTH following placebo. The percent change in area over the curve (ΔAOC) was defined as the cumulative percent decrement from baseline value to the experimental values over 6 hours following test loads (Heller, 2000), where a negative value for ΔAOC represented overall parathyroid suppression.

ΔAOC of serum PTH was −118% with EffCaMgCit, −82% with milk and +7% with placebo. ΔAOC was significantly different between EffCaMgCit and placebo (p=0.001) and between milk and placebo (p=0.02). The difference in ΔAOC was significantly different between phases by ANOVA (p=0.0001). Thus, EffCaMgCit produced a relatively greater parathyroid suppression than milk.

Example 6

Superior Calcium Bioavailability of EffCaMgCit over Calcium Carbonate before and Following Proton Pump Inhibitor Therapy In this PPI protocol, the bioavailability of calcium and magnesium was compared between EffCaMgCit and calcium carbonate to test the hypothesis that EffCaMgCit confers adequate calcium and magnesium bioavailability even when gastric acid secretion is inhibited by omeprazole (a common PPI drug) therapy, whereas calcium carbonate does not. This hypothesis was based on the finding that the solubility of calcium carbonate is dependent on pH of gastric fluid (Pak, 1989) whereas EffCaMgCit is pre-solubilized before ingestion, and that EffCaMgCit contains magnesium whereas calcium carbonate does not.

Figure 4:
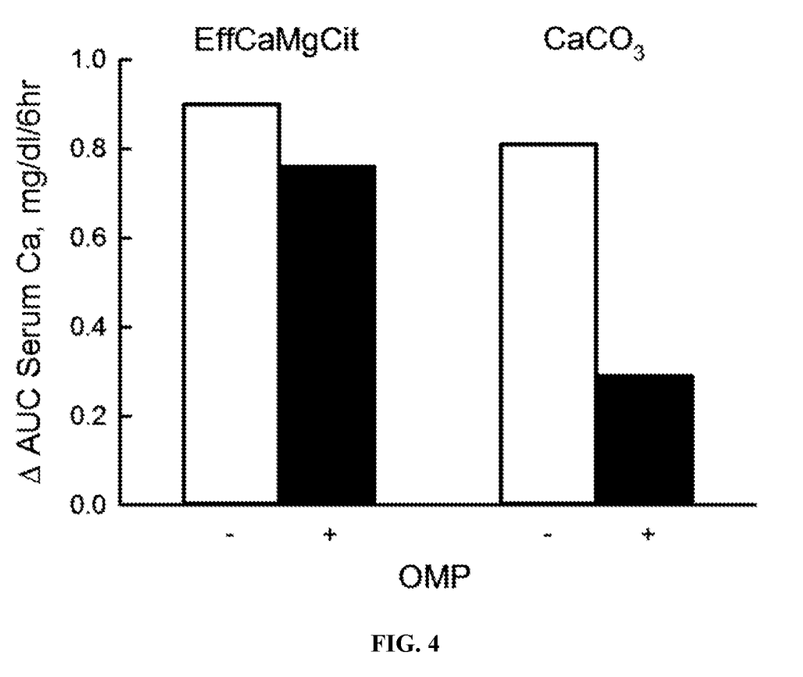
Figure 5:
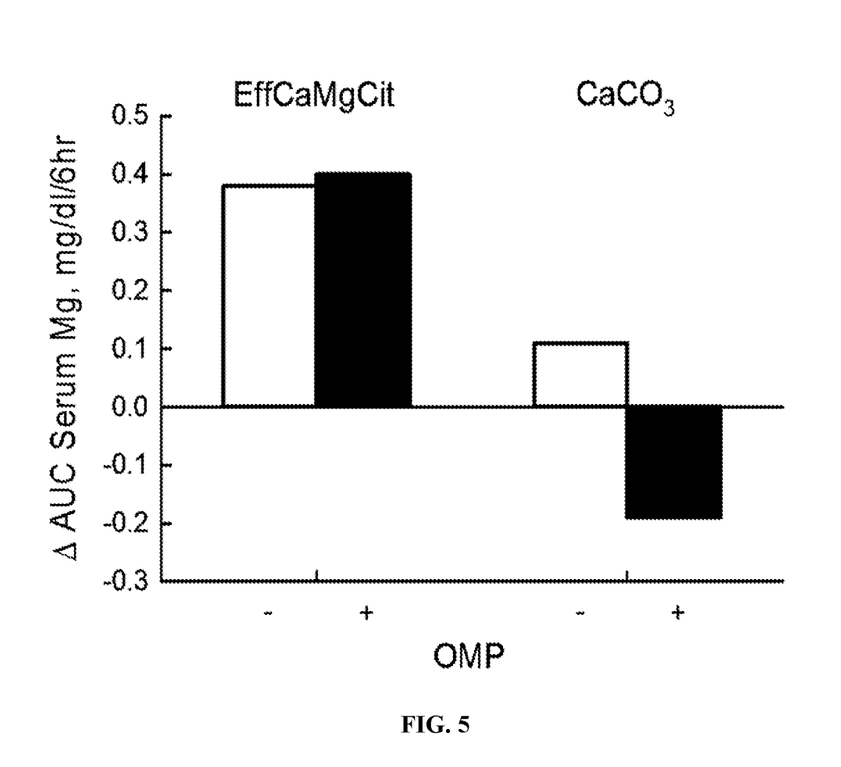
FIG. 5 shows intestinal magnesium absorption from a single load of EffCaMgCit or calcium carbonate on the $7^{th}$ day of treatment with OMP (+OMP) or placebo (−OMP) in 11 adult men or women from the same study as in FIG. 4. Intestinal magnesium absorption was measured from the cumulative increment in serum magnesium from baseline ($\Delta AUC$ of serum magnesium) over 6 hours following test loads.
Figure 6:
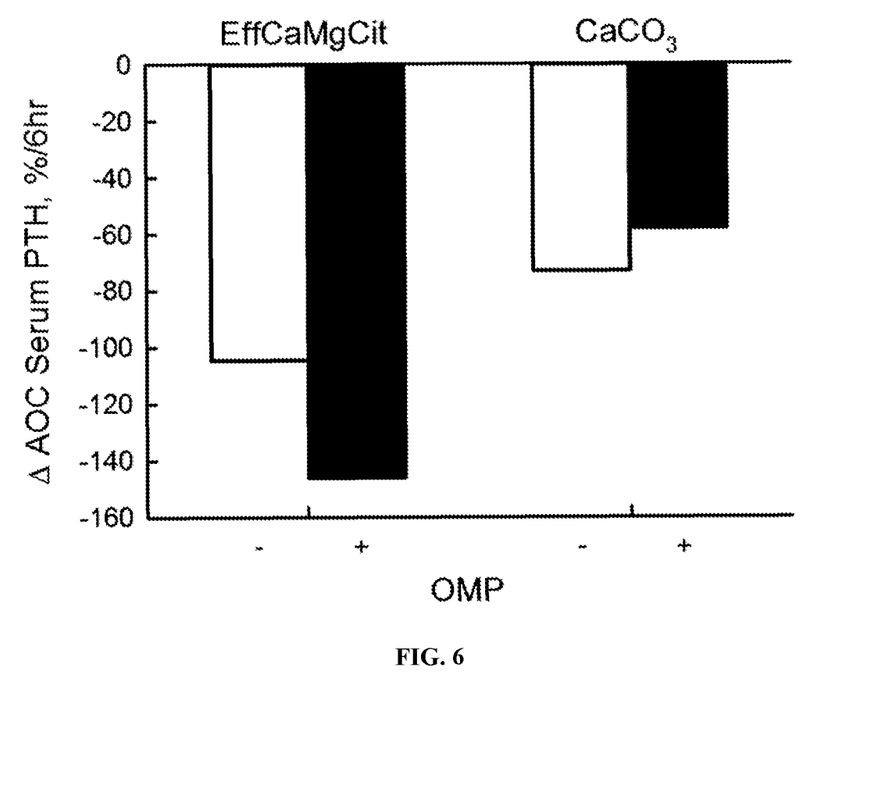
FIG. 6 shows parathyroid suppression from a single load of EffCaMgCit or calcium carbonate on the $7^{th}$ day of treatment with OMP (+OMP) or placebo (−OMP) from the same study as in FIG. 4. Change in area over the curve ($\Delta AOC$) of serum PTH was defined as the percent decrement in serum PTH from baseline to the experimental values during 6 hours following EffCaMgCit or calcium carbonate loads (Heller, 2000). A negative value for $\Delta AOC$ indicates a decline in serum PTH or parathyroid suppression.

Eleven adult men or women completed four phases of study in a randomized crossover design. After taking omeprazole (20 mg) or placebo twice per day for a week, each subject underwent a single dose bioavailability study with EffCaMgCit or calcium carbonate. The four phases were: EffCaMgCit on omeprazole, calcium carbonate on omeprazole, EffCaMgCit on placebo, and calcium carbonate on placebo. EffCaMgCit load delivered 400 mg (20 meq) calcium, 122 mg (10 meq) magnesium and 50 meq citrate. Calcium carbonate load gave 400 mg calcium but no magnesium or citrate. Before and hourly for 6 hours after the test load, a venous blood sample was obtained for calcium, magnesium and PTH. A limited number of subjects precluded delineation of definitive statistical differences. However, a discernible trend was disclosed as shown in FIGS. 4-6.

From the change in serum calcium from baseline during 6 hours after the test load, the change in area over the curve (ΔAUC) was calculated as a measure of intestinal calcium absorption (Heller, 2000). After taking placebo (instead of omeprazole) for a week, ΔAUC of serum calcium following EffCaMgCit load was slightly higher than from calcium carbonate (FIG. 4). On omeprazole therapy, ΔAUC of serum calcium following EffCaMgCit load declined non-significantly by 16% from the value obtained after placebo load (without omeprazole). However, ΔAUC of serum calcium from calcium carbonate load decreased substantially by 64% on omeprazole compared to placebo.

Thus, calcium bioavailability from EffCaMgCit is not affected by inhibition of gastric acid secretion, probably owing to the delivery of soluble calcium. In contrast, calcium bioavailability from calcium carbonate is impaired by PPI treatment, attesting to the dependence of solubility of calcium carbonate on gastric acid secretion.

Example 7

Provision of Bioavailable Magnesium by EffCaMgCit during PPI Therapy

From the same PPI protocol as Example 6, ΔAUC of serum magnesium, a measure of bioavailable magnesium, was calculated from the change in serum magnesium concentration from baseline during 6 hours after a single oral load of EffCaMgCit or calcium carbonate. On placebo (without omeprazole), ΔAUC of serum magnesium after EffCaMgCit was substantial, with a cumulative increase of 0.38 mg/dL and peak increase of 0.13 mg/dL (FIG. 5). On omeprazole, ΔAUC of serum magnesium after EffCaMgCit did not change much from placebo. However, ΔAUC of serum magnesium after calcium carbonate was negligible on both placebo and omeprazole. The difference in ΔAUC between the two salts on omeprazole treatment was significant (p=0.03).

Thus, EffCaMgCit provides bioavailable magnesium even when gastric acid secretion is inhibited, owing to the delivery of soluble magnesium. In contrast, calcium carbonate does not provide bioavailable magnesium, since it does not contain magnesium.

Example 8

Parathyroid Suppression by EffCaMgCit during PPI Therapy

In the same PPI protocol as Example 6, parathyroid suppression was compared between EffCaMgCit and calcium carbonate while on placebo (without omeprazole) or on omeprazole therapy. The change in area over the curve (ΔAOC) was obtained from the cumulative percent decrement in serum PTH from baseline to the experimental values over 6 hours following a single oral dose of EffCaMgCit or calcium carbonate (Heller, 2000). A negative value for ΔAOC indicated cumulative decline in serum PTH from baseline, or parathyroid suppression.

After EffCaMgCit load, ΔAOC of serum PTH was negative following both placebo (−105%) and omeprazole (−146%); the difference was not significant (FIG. 6). After calcium carbonate load, ΔAOC of serum PTH was also negative during both placebo and omeprazole treatment. On both placebo and omeprazole, ΔAOC was more negative after EffCaMgCit than after calcium carbonate; the difference in ΔAOC between the two salts during omeprazole treatment was significant (p=0.003). The difference in ΔAOC between phases was significant by ANOVA (p=0.02). The changes in serum PTH were generally opposite in direction to those for serum calcium.

Thus, EffCaMgCit suppresses parathyroid function even after inhibition of gastric acid secretion; this effect of EffCaMgCit is greater than that of calcium carbonate.

* * *

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bolland et al., *Brit. Med. J.*, 342:2040, 2011.
Byer and Khan, *J. Urol.*, 173:640-646, 2005.
Cunha et al., *J. Am. Soc. Hyperten.*, online, 2013.
Ewence et al., *Circ. Res.*, 103: e28-34, 2008.
Hamano et al., *J. Am. Soc. Nephrol.*, 21:1998-2007, 2010.
Heiss et al., *Biophy. J.*, 99:3986-3995, 2010.
Heller et al., *J. Clin. Pharm.*, 40:1237-1244, 2000.
Kircelli et al., *Nephrol. Dialy. Transplant.*, 27:514-521, 2012.
Kok et al., *Lancet*, i: 1056-1058, 1986.
Kuipers et al., *Netherl. J. Med.*, 67: 169-172, 2009.
Li et al., *Heart*, 98:920-925, 2012.
Montezuno et al., *Hypertension*, 56:453-462, 2010.
O'Connell et al., *Am. J. Med.*, 118: 778-781, 2005.
Pak et al., *J. Clin. Endoc. Metab.*, 65:801-805, 1987.
Pak et al., *J. Bone Min. Res.*, 4:119-127, 1989.
Pasch et al., *J. Am. Soc. Nephrol.*, 23: 1744-1752, 2012.
Reid et al., *Osteop. Int.*, 22:1649-1658, 2011.
Reynolds et al., *J. Am. Soc. Nephrol.*, 15:2857-2867, 2004.
Roux et al., *Calcif. Tissue Int.*, 84:13-19, 2009.
Sage et al., *Kid. Int.*, 79:414-22, 2011.

The invention claimed is:

1. A method of reducing calciprotein particle (CPP) formation in an animal in need thereof, the method comprising:
administering to the animal a composition comprising:
from about 250 mg calcium to about 600 mg of calcium,
from about 70 mg magnesium to about 175 mg of magnesium,
at least 10 meq of citrate excess, and
at least 20 meq of total soluble citrate,
wherein the Ca/citrate molar ratio is from 0.4 to 0.7 and wherein the CPP formation is reduced.

2. The method of claim 1, wherein the serum magnesium is increased in the animal.

3. The method of claim 1, wherein the serum phosphate is reduced in the animal.

4. The method of claim 1, wherein hyperparathyroidism is reduced in the animal.

5. The method of claim 1, wherein the composition comprises 300 mg of calcium, 122 mg of magnesium, 20 meq of citrate excess, and 45 meq of total soluble citrate, wherein the Ca/citrate molar ratio is about 0.5.

6. The method of claim 1, wherein the composition consists essentially of 300 mg of calcium, 122 mg of magnesium, 20 meq of citrate excess, and 45 meq of total soluble citrate, wherein the Ca/citrate molar ratio is about 0.5.

7. The method of claim 1, wherein the composition consists of 300 mg of calcium, 122 mg of magnesium, 20 meq of citrate excess, and 45 meq of total soluble citrate, wherein the Ca/citrate molar ratio is about 0.5.

8. The method of claim 1, wherein the alkali load is increased in the animal.

9. The method of claim 1, wherein the animal is a human.

10. The method of claim 9, wherein the human has been diagnosed with chronic kidney disease (CKD).

11. The method of claim 10, wherein the CKD is stage 5 CKD.

* * * * *